US008989347B2

(12) United States Patent
Sperl et al.

(10) Patent No.: US 8,989,347 B2
(45) Date of Patent: Mar. 24, 2015

(54) IMAGE RECONSTRUCTION METHOD FOR DIFFERENTIAL PHASE CONTRAST X-RAY IMAGING (71) Applicant: General Electric Company, Schenectady, NY (US)

(72) Inventors: Jonathan Immanuel Sperl, Freising (DE); Dirk Wim Jos Beque, Munich (DE)

(73) Assignee: General Electric Company, Niskayuna, NY (US)

( * ) Notice: Subject to any disclaimer, the term of this patent is extended or adjusted under 35 U.S.C. 154(b) by 273 days.

(21) Appl. No.: 13/719,815

(22) Filed: Dec. 19, 2012

(65) Prior Publication Data
US 2014/0169524 A1 Jun. 19, 2014

(51) Int. Cl.
G06T 7/00 (2006.01)
G01N 23/04 (2006.01)
G06T 5/00 (2006.01)

(52) U.S. Cl.
CPC ............ G06T 5/001 (2013.01); G01N 23/046 (2013.01); *G01N 2223/419* (2013.01); *G01N 2223/612* (2013.01)
USPC .......... 378/62; 378/87; 250/370.08; 382/254; 382/132

(58) Field of Classification Search
CPC .... A61B 6/484; A61B 6/4291; A61B 6/4035; A61B 6/06; G01N 2223/401; G01N 23/046; G01N 23/06; G06T 5/001
USPC ........... 378/62, 87; 250/370.08; 382/254, 132
See application file for complete search history.

(56) References Cited

U.S. PATENT DOCUMENTS

| 4,845,352 A | 7/1989 | Benschop |
| 7,433,444 B2 | 10/2008 | Baumann et al. |
| 7,440,542 B2 | 10/2008 | Baumann et al. |
| 7,453,981 B2 | 11/2008 | Baumann et al. |
| 7,486,770 B2 | 2/2009 | Baumann et al. |
| 7,492,871 B2 | 2/2009 | Popescu et al. |
| 7,522,698 B2 | 4/2009 | Popescu et al. |

(Continued)

FOREIGN PATENT DOCUMENTS

| DE | 102009018882 A1 | 10/2010 |
| WO | 2007074029 A1 | 7/2007 |

(Continued)

OTHER PUBLICATIONS

Kottler, C., et al.; "A two-directional approach for grating based differential phase contrast imaging using hard x-rays", Optics Express,, vol. 15, No. 3, pp. 1175-1181, Feb. 2007.

(Continued)

*Primary Examiner* — Nikita Wells
(74) *Attorney, Agent, or Firm* — Fletcher Yoder, P.C.

(57) ABSTRACT

A phase retrieval method for differential phase contrast imaging includes receiving data corresponding to a differential phase image generated from a measured signal. The measured signal corresponds to an X-ray signal detected by a detector after passing through a subject located with a grating arrangement between an X-ray source and the detector. The method further includes generating a phase image corresponding to the integration of the differential phase image. Generating the phase image includes performing an iterative total variation regularized integration in the Fourier domain.

17 Claims, 5 Drawing Sheets

(56) References Cited

U.S. PATENT DOCUMENTS

| | | |
|---|---|---|
| 7,522,708 B2 | 4/2009 | Heismann et al. |
| 7,532,704 B2 | 5/2009 | Hempel |
| 7,535,986 B2 | 5/2009 | Hempel |
| 7,564,941 B2 | 7/2009 | Baumann et al. |
| 7,639,786 B2 | 12/2009 | Baumann et al. |
| 7,645,018 B2 | 1/2010 | Ikushima |
| 7,646,843 B2 | 1/2010 | Popescu et al. |
| 7,653,177 B2 | 1/2010 | Baumann et al. |
| 7,889,838 B2 | 2/2011 | David et al. |
| 7,920,673 B2 | 4/2011 | Lanza et al. |
| 7,924,973 B2 | 4/2011 | Kottler et al. |
| 7,945,018 B2 | 5/2011 | Heismann et al. |
| 7,949,095 B2 | 5/2011 | Ning et al. |
| 7,983,381 B2 | 7/2011 | David et al. |
| 8,005,185 B2 | 8/2011 | Popescu |
| 8,009,796 B2 | 8/2011 | Popescu |
| 8,165,270 B2 | 4/2012 | David |
| 8,233,587 B2 | 7/2012 | Sato |
| 8,243,879 B2 | 8/2012 | Itoh |
| 8,306,183 B2 | 11/2012 | Koehler |
| 8,351,570 B2 | 1/2013 | Nakamura |
| 8,374,309 B2 | 2/2013 | Donath |
| 8,520,217 B2 | 8/2013 | Noai |
| 8,767,916 B2 * | 7/2014 | Hashimoto et al. ............. 378/62 |
| 2010/0322380 A1 | 12/2010 | Baeumer et al. |
| 2011/0013743 A1 | 1/2011 | Nakamura |
| 2011/0051889 A1 | 3/2011 | Sato |
| 2011/0261924 A1 | 10/2011 | Bredno |
| 2011/0311024 A1 | 12/2011 | Koehler |
| 2012/0008747 A1 | 1/2012 | Roessl et al. |
| 2012/0020461 A1 | 1/2012 | Roessl et al. |
| 2012/0057677 A1 | 3/2012 | Vogtmeier et al. |
| 2012/0099702 A1 | 4/2012 | Engel |
| 2012/0275564 A1 * | 11/2012 | Hashimoto ..................... 378/62 |
| 2014/0185757 A1 * | 7/2014 | Sperl et al. ..................... 378/62 |

FOREIGN PATENT DOCUMENTS

| | | |
|---|---|---|
| WO | 2010150136 A1 | 12/2010 |
| WO | 2011011014 A1 | 1/2011 |
| WO | 2012029039 A1 | 3/2012 |

OTHER PUBLICATIONS

Donath, Tilman, et al.; "Towards clinical X-ray phase-contrast CT", Invest. Radiol. 2010, 6 pages.

Burvall, Anna, et al.; "Phase retrieval in Xx-ray phase-contrast imaging suitable for tomography", Optics Express vol. 19, No. 11, May 2011, pp. 10359-10376.

Kneip, S., et al.; "X-ray phase contrast imaging of biological specimens with tabletop synchrotron radiation", Nature Procedings:hdl:10101/npre,2011.5948.1:posted May 12, 2011, 10 pages.

Thuring, Thomas, et al.; "Non-linear regularized phase retrieval for unidirectional X-ray differential phase contrast radiography", Optics Express, vol. 19, No. 25, Dec. 2011, pp. 25545-25558.

* cited by examiner

IMAGE RECONSTRUCTION METHOD FOR DIFFERENTIAL PHASE CONTRAST X-RAY IMAGING

BACKGROUND

The subject matter disclosed herein generally relates to X-ray imaging techniques and, in particular, to systems and methods for reconstructing images in X-ray phase contrast imaging.

In non-invasive imaging systems, X-ray tubes are used in various X-ray systems and computed tomography (CT) systems as a source of X-ray radiation. The radiation is emitted in response to control signals during an examination or imaging sequence. Typically, the X-ray tube includes a cathode and an anode. An emitter within the cathode may emit a stream of electrons in response to heat resulting from an applied electrical current, and/or an electric field resulting from an applied voltage to a properly shaped metallic plate in front of the emitter. The anode may include a target that is impacted by the stream of electrons. The target may, as a result of impact by the electron beam, produce X-ray radiation to be emitted toward an imaged volume.

Conventional X-ray imaging systems may detect an imaged volume based on absorption of the X-ray radiation. However, absorption-based techniques may provide images with insufficient distinction between certain types of tissue structures. For example, tumors and fluid-filled cysts may be difficult to distinguish on images generated by X-ray absorption of tissue. Other techniques, such as phase contrast techniques, may provide images with more contrast between different types of tissue structures. However, image reconstruction associated with such techniques may be subject to a variety of drawbacks associated with factors such as image geometry, hardware constraints, and so forth.

For example, in grating based differential X-ray phase contrast techniques, the obtained measurement generates projections of the gradient of the cumulative phase shift due to refractive index variability of the subject in a direction orthogonal to the X-ray beam and to the grating slits, thus resulting in projections that have a differential nature. In order to visualize these projections for diagnostic purposes, an integration step is required. Unfortunately, the noisy nature of the data may complicate the integration step, thereby resulting in blurred images having streak artifacts along the line of integration. Accordingly, there exists a need for imaging and methods that address these drawbacks.

BRIEF DESCRIPTION

In one embodiment, a phase retrieval method for differential phase contrast imaging includes receiving data corresponding to a differential phase image generated from a measured signal. The measured signal corresponds to an X-ray signal detected by a detector after passing through a subject located with a grating arrangement between an X-ray source and the detector. The method further includes generating a phase image corresponding to the integration of the differential phase image. Generating the phase image includes performing an iterative total variation regularized integration in the Fourier domain.

In another embodiment, an X-ray imaging system for differential phase contrast imaging of a subject includes an X-ray source that in operation generates an X-ray beam directed toward the subject and a detector that in operation detects at least a portion of the X-ray beam and produces a signal corresponding to the detected portion of the X-ray beam. The system also includes a grating system having a source grating located between the X-ray source and the subject, and a phase grating and an analyzer grating each located between the subject and the detector. In operation, a controller receives the signal from the detector, performs a reconstruction of a differential phase image of the subject based on the signal, and generates a phase image corresponding to the integration of the differential phase image. The controller performs an iterative total variation regularized integration in the Fourier domain to generate the phase image.

In another embodiment, an image reconstruction method for differential phase contrast imaging includes receiving data corresponding to a signal produced by an X-ray detector and corresponding to X-rays that passed through a subject and a grating system to reach the X-ray detector. The method also includes generating a differential phase image of the subject based on the received data and generating a phase image corresponding to the integration of the differential phase image by performing an iterative total variation regularized integration in the Fourier domain to generate the phase image.

In another embodiment, a non-transitory computer readable medium encoding one or more executable routines, which, when executed by a processor, cause the processor to perform acts including performing an image reconstruction of a phase image of a subject based on a signal generated by an X-ray detector based on a detected X-ray beam that passed through a subject and a grating system. Performing the image reconstruction includes generating a differential phase image of the subject based on the signal and performing an iterative total variation regularized integration in the Fourier domain to generate the phase image from the differential phase image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Provided herein are phase retrieval systems and methods for differential X-ray phase contrast (XPC) imaging that enable a phase image of a subject to be generated from a differential phase image of the subject. Since the measurement principle in differential XPC imaging is based on the refraction of an X-ray beam penetrating through matter, projections of the gradient of the cumulative phase shift due to the refractive index variability of the subject are generated in a direction orthogonal to the X-ray beam. The differential XPC projections have a differential nature because of this gradient, and thus, require integration to obtain a phase image of the subject. Presently disclosed embodiments may offer advantages over systems that perform a one dimensional integration step in the image domain to obtain the phase image from the differential phase image. For example, in certain embodiments, by applying an iterative reconstruction technique in the Fourier domain, the low frequency character of the image noise may be better addressed, thus resulting in phase images of increased resolution and reduced blurring compared to conventional methods. These and other features of presently disclosed embodiments are described in more detail below.

Figure 1:
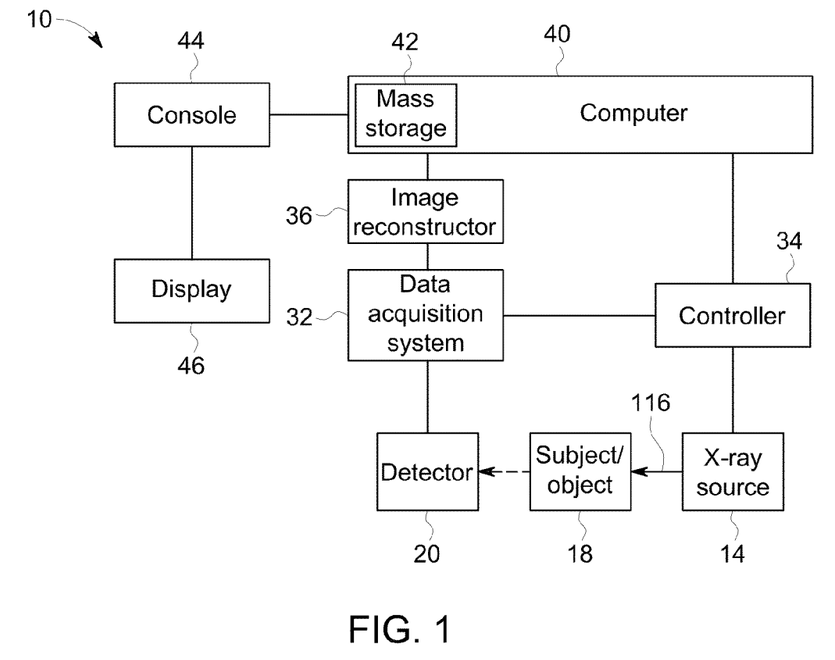
FIG. 1 is a block diagram illustrating an embodiment of an X-ray imaging system.

Turning now to the drawings, FIG. 1 illustrates an X-ray imaging system 10 including an X-ray source 14 that projects a beam of X-rays 16 through a subject 18 (e.g., a patient, object, sample, etc.) toward one or more detectors 20. The detector 20 is coupled to a data acquisition system 32. The one or more detectors 20 sense the transmitted X-rays that pass through the subject 18, and the data acquisition system 32 converts the sensed X rays to digital signals for subsequent processing. Each detector 20 produces an electrical signal that represents the intensity of an impinging X-ray beam after it passes through the subject 18. The operation of the X-ray source 14 may be governed by an X-ray controller 34 that provides power and timing signals to the X-ray source 14. An image reconstructor 36 receives sampled and digitized X-ray data from the data acquisition system 32 and performs reconstructions to produce phase contrast images. The reconstructed image is applied as an input to a processor-based computer 40 that stores the image in a mass storage device 42.

The computer 40 also receives commands and scanning parameters from an operator via a console 44 that has some form of operator interface, such as a keyboard, mouse, voice activated controller, or any other suitable input apparatus. An associated display 46 enables the operator to observe the reconstructed images and other data from the computer 40. The operator-supplied commands and parameters are used by the computer 40 to provide control signals and information to the data acquisition system 32 and the X-ray controller 34.

Figure 2:
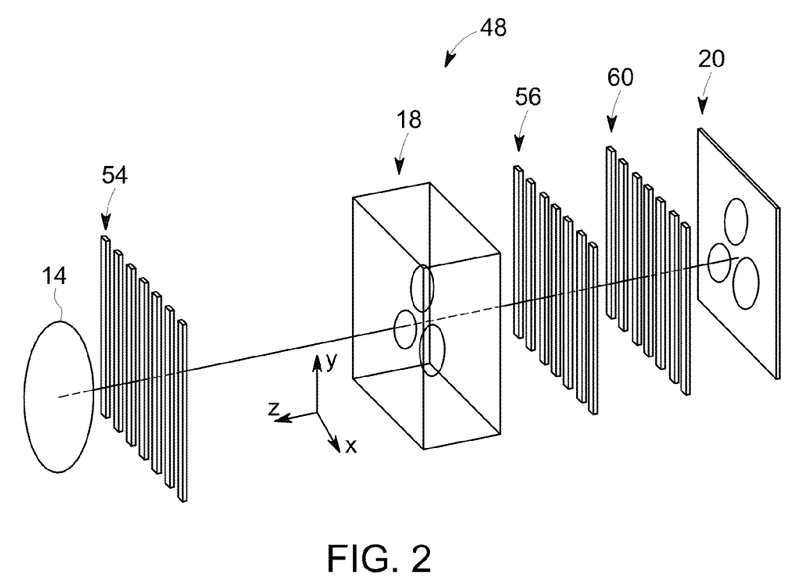
FIG. 2 is a schematic illustrating an example X-ray beam path in a grating based phase contrast imaging operation in accordance with an embodiment.

FIG. 2 illustrates a differential XPC imaging setup 48 in which a spatially coherent X-ray beam is used to probe an object (or subject) 18. In the illustrated embodiment, an incoherent X-ray source 14 is provided with a blocking grating 54 to create the coherent X-ray beam. However, in other arrangements, the spatially coherent X-ray beam may be realized by synchrotron radiation, a micro focus X-ray source, or any other suitable source. In the illustrated embodiment, the spatially coherent X-ray beam passes a phase grating 56, and periodic interference patterns or fringes are generated. Since their period is typically in the order of a few μm, an interferometric technique is applied to analyze the fringes using an X-ray detector 20 (e.g., having a pixel in the order of a few 100 μm). Another blocking grating 60 having the same period as the fringes is placed in front of the detector 20.

During operation of the illustrated imaging setup 48, in a series of steps, grating 60 is shifted by a fraction of its period in the direction orthogonal to the grating slits, and images are taken for each position. After covering the entire period, the measurements for each detector pixel may be described as the convolution of the fringes with the rectangular grating function. Using Fourier analysis, the phase of the fringes are determined During an imaging operation, in addition to the gratings 56 and 60, the object or subject 18 is placed into the X-ray beam, and the X-rays are refracted by the object 18 and hence undergo an additional phase shift. By repeating the measurement procedure, the phase of the shifted fringes is detected and the difference of both measurements yields the phase shift due to the object 18. In other words, the differential XPC measurement generates projections of the gradient of the cumulative phase shift due to refractive index variability of the object in a direction orthogonal to the X-ray beam and to the grating slits.

Figure 3:
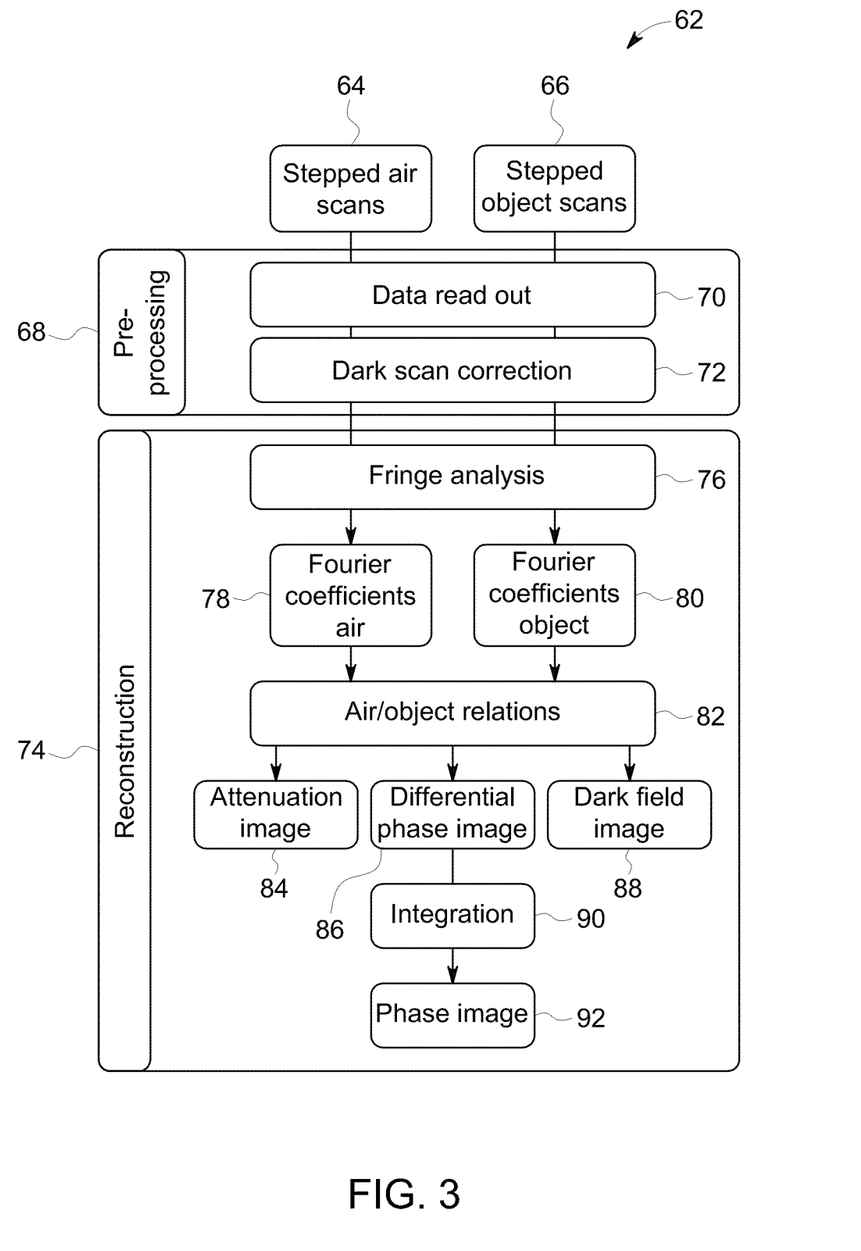
FIG. 3 is a block diagram illustrating an embodiment of an image reconstruction process for a phase contrast X-ray imaging operation.

Once measured signals are obtained in this manner, data processing and reconstruction of phase images may be performed to obtain diagnostically useful images. FIG. 3 illustrates an embodiment of a method 62 that may be employed, for example, by controller 34 or image reconstructor 36, to obtain one or more images of the object 18. More specifically, the method 62 calls for one or more stepped air scans 64 and one or more stepped object scans 66 to be performed, for example, in accordance with the steps described above with respect to the imaging setup 48. During pre-processing 68, the data obtained from the scans 64 and 66 is read out (block 70), and a dark scan correction is performed (block 72) to normalize for the noise introduced into the system by features of the detector 20.

During image reconstruction 74, the data corresponding to the signals measured by the detector is processed to obtain the desired images. In the illustrated embodiment, a fringe analysis (block 76) is performed to process the interference patterns generated during the imaging procedure when the X-rays interacted with the object 18 and the gratings 56 and 60. For example, since the measurement signal represents the convolution of the generated signal with the grating function, characterization of the obtained curve is performed to determine the offset, amplitude, and phase. A variety of implementation-specific steps may occur during the fringe analysis, such as but not limited to computation of the zeroth and first order Fourier coefficients. Accordingly, the fringe analysis (block 76) outputs include Fourier coefficients 78 corresponding to the air scans 64 and Fourier coefficients 80 corresponding to the object scans 66.

In the illustrated embodiment, the Fourier coefficients 78 and 80 are then used to perform an air/object relation step (block 82) in which features of the air scan 64 are compared to features of the object scan 66 to obtain clinically relevant information. That is, the data from the air scan 64 may be used as a baseline for comparison with the data from the object scan 66 to determine the phase shift contributed by the object 18. Accordingly, an attenuation image 84, a differential phase image 86, and a dark field image 88 are produced in the depicted image reconstruction 74. However, it should be noted that in other embodiments, only select images may be produced, depending on implementation-specific considerations. Further, as mentioned above, in order to visualize the differential XPC projections in a manner that is in accordance with conventional diagnostics, it may be desirable to integrate the differential phase image 86 (block 90) to generate a phase image 92 of the imaged object 18.

In some conventional systems, integrating the differential phase image 86 to generate the phase image 92 results in blurring and/or streaking due to the noisy nature of the data, and a low resolution phase image may be obtained. Provided herein are iterative total variation reconstruction techniques applied in the Fourier domain and when applied to the differential phase image 86, may reduce the likelihood that the phase image 92 has low resolution, streaking, and/or blurring. In particular, certain embodiments of the disclosed techniques include an iterative reconstruction applied in the Fourier domain making use of the Fourier representation of the integration operator and restricting regularization to the low-frequency domain.

That is, as described in more detail below, provided herein are embodiments of a Fourier domain technique for total variation regularized phase retrieval. Embodiments of this technique are an iterative reconstruction process that makes use of the two dimensional character of the measured data and utilizes the concept of total variation regularization in the Fourier domain instead of in the image domain. Accordingly, certain embodiments may enable frequency dependent regularization, for example, restricting regularization to the low-frequency domain. The foregoing feature may give rise to one or more advantages over current systems, such as a reduction of streak artifacts without increasing image blurring.

In one embodiment, a differential XPC measurement yields differential phase values $\psi=\partial_x\phi$ with $\partial_x$ the gradient along x. Hence, the phase reconstruction task denotes the determination of $\phi$ given noisy measurements $\psi$. It can be stated in Fourier domain (with spatial frequency $\omega$) as:

$$F_x(\psi)=wF_x(\phi) \text{ with } w=w(\omega)=j\omega, \quad (1)$$

and $F_x$ the one dimensional Fourier transform along x. Set $a:=F_x(\phi)$ and formulate the reconstruction task as:

$$\min_a \|F_x^{-1}(wa)-\psi\| + \lambda TV_{y,\tilde{w}}(a), \quad (2)$$

with $TV_{y,\tilde{w}}(a)$ being the weighted total variation of a along y, i.e., in Fourier domain and orthogonal to the direction of integration x, with a weighting function $\tilde{w}(\omega)$. That is, minimization of a residual norm may be supplemented by adding one or more weighted regularization terms. Due to this weighting function, frequency dependent regularization may be employed in some embodiments. For example, in one embodiment, regularization may be restricted to the low frequency domain. That is, in certain embodiments, a weighting term associated with low frequency characteristics may be substantially greater than a weighting term associated with high frequency characteristics. In this manner, presently disclosed embodiments enable a weighting function (e.g., the rectangular weighting function) to be used to apply frequency dependent regularization.

In presently disclosed embodiments, the optimization problem in (1) is addressed by an iterative shrinking process employing total variation regularization. Starting with an initial solution $a_1$ (e.g., the Fourier transform of the solution of a standard forward integration method), the t-th iteration of the process reads (for $A:=F_x^{-1}w$):

$$z^t = Aa^t \quad (3)$$

$$c^t = A^H z^t + a^t \quad (4)$$

$$a^{t+1} = c^t + \sigma_t \tilde{w} \frac{\nabla_y c^t}{\|\nabla_y c^t\|}, \quad (5)$$

where $\sigma_t$ denotes a scalar weighting that may vary over the iterations.

Figure 4:
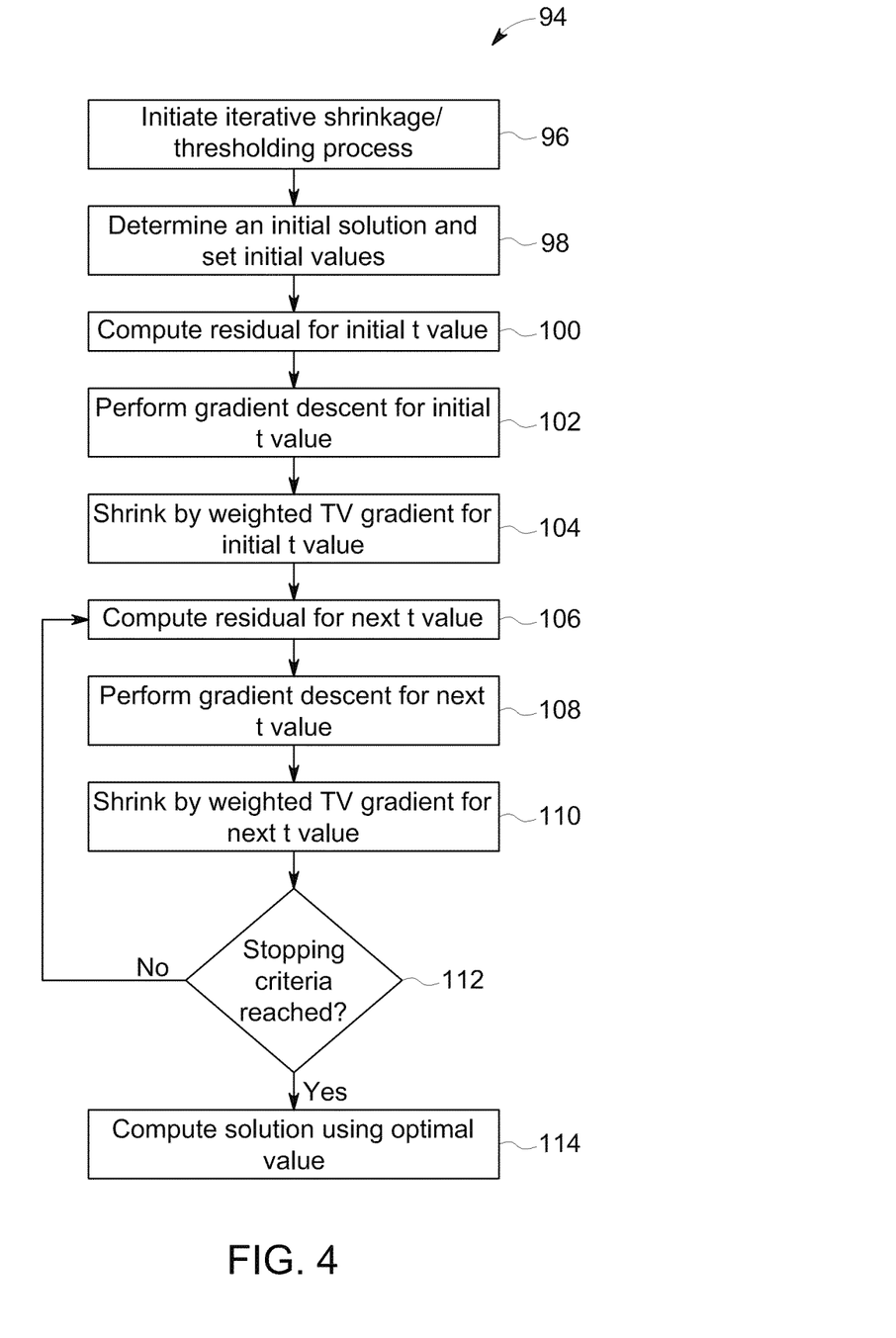
FIG. 4 is a flow chart illustrating an embodiment of a total variation iterative shrinkage/thresholding method implemented in the Fourier domain.

One embodiment of the above-described method is shown in the flow chart 94 of FIG. 4. The method 94 begins with an initiation of the iterative shrinkage/thresholding process (block 96) and proceeds to a determination of an initial solution and setting of initial values (block 98). The initial conditions for the iterative process may be obtained in any implementation-specific manner, for example, by using values dictated by traditional methods as a starting point. The method 94 proceeds by computing a residual for the chosen initial value (block 100). For example, equation (3) may be applied in this step. The process continues by performing a gradient descent for the initial value (block 102) and shrinking by a weighted total variation gradient for the initial value (block 104), for example, by applying equations (4) and (5), respectively.

This process continues in an iterative fashion for all the desired t values. Specifically, the residual is computed for the next t value (block 106), for example using equation (3). The method 94 then calls for performing a gradient descent in accordance with equation (4) for the next t value (block 108) and shrinking by a weighted total variation gradient for the next t value (block 110). The method 94 includes an inquiry as to whether a stopping criteria has been reached (block 112). For example, in one embodiment, the inquiry 112 may include inquiring as to if the final t value has been reached. If the final t value has not been reached, the method 94 proceeds in an iterative fashion through the t values. However, if they final iteration has been performed, the solution is computed using the final a opt (block 114). However, it should be noted that the stopping criteria may be any suitable implementation-specific criteria. For instance, in another embodiment, the stopping criteria may include determining if the change of the norm of the residual is below a preset threshold.

Figure 5A:
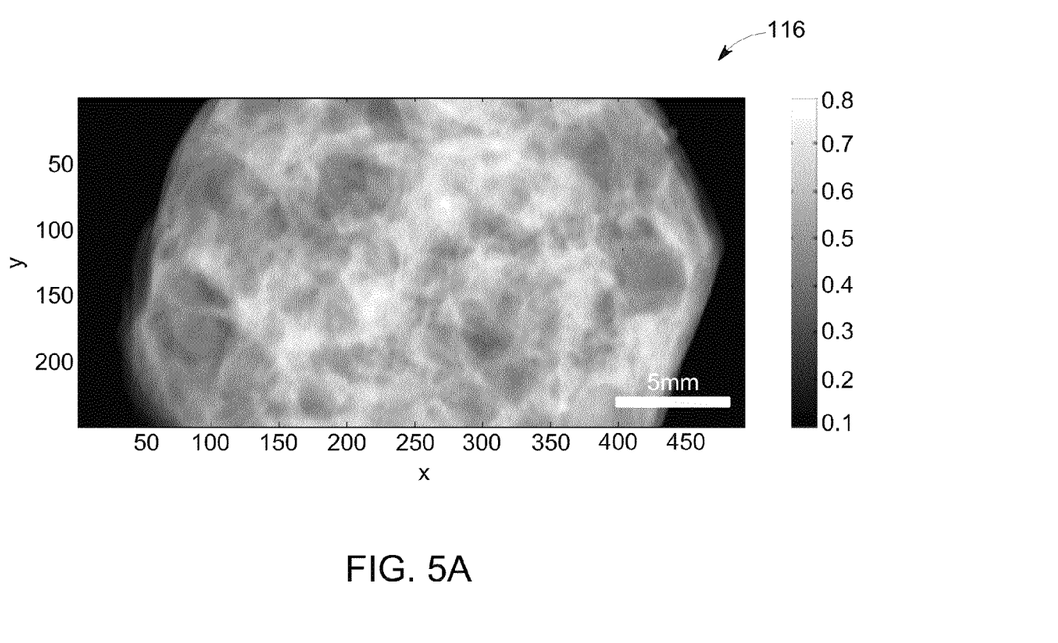
FIG. 5A illustrates an absorption-based X-ray image in accordance with an embodiment.
Figure 5B:
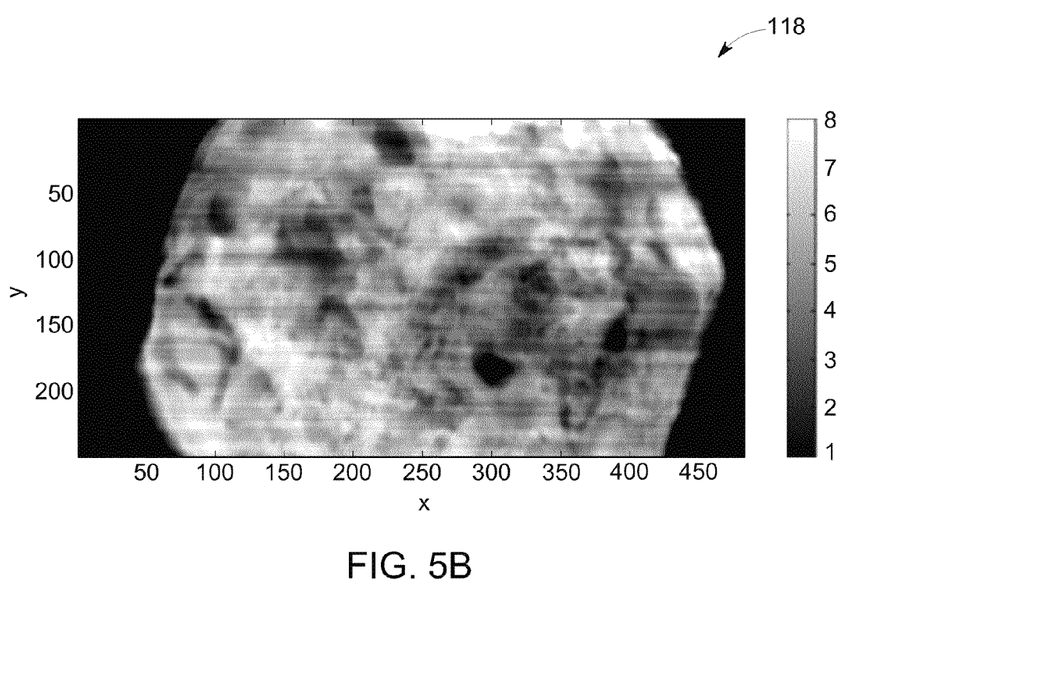
FIG. 5B illustrates an X-ray image reconstructed using standard integration in accordance with an embodiment.
Figure 5C:
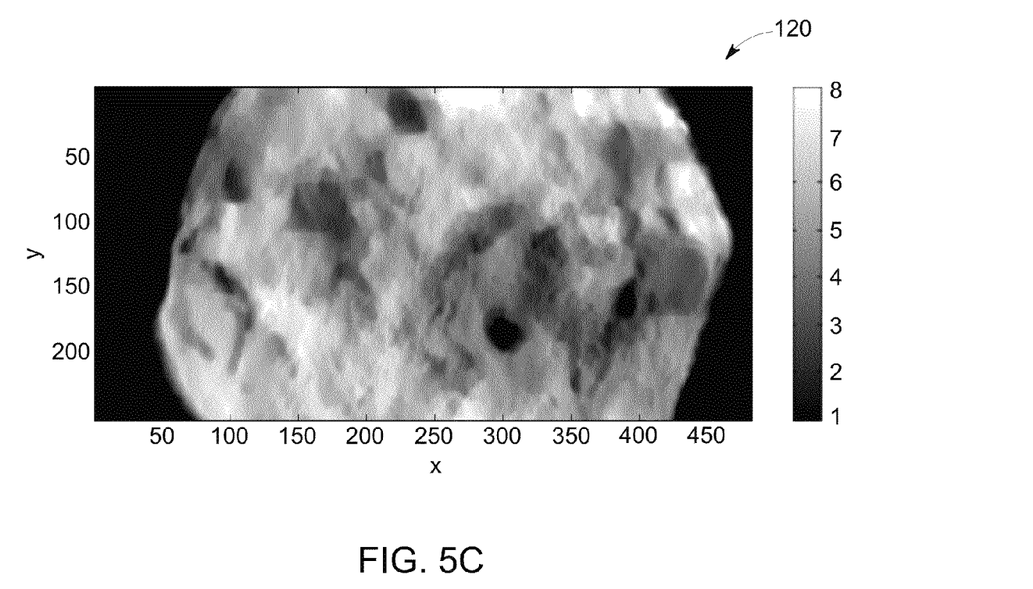
FIG. 5C illustrates an X-ray image reconstructed using total variation regularization methods in the image domain in accordance with an embodiment.
Figure 5D:
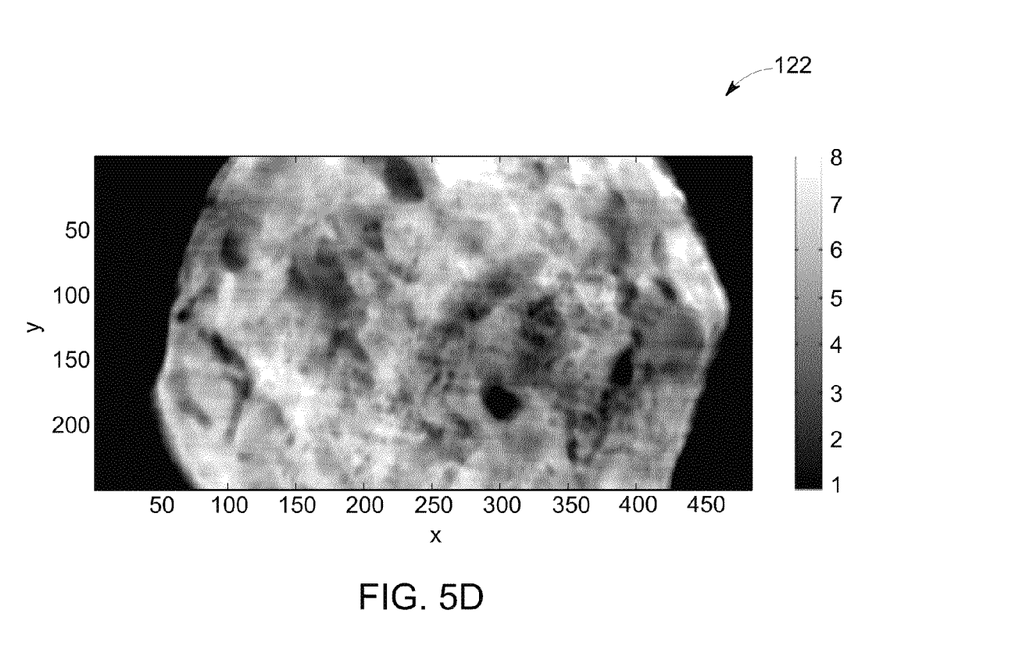
FIG. 5D illustrates an X-ray image reconstructed using total variation regularization methods in the Fourier domain in accordance with an embodiment.

FIGS. 5A-D illustrate phase images corresponding to data acquired for a 5 mm thick salami slice on a differential XPC imaging system and reconstructed using different methods. More specifically, FIG. 5A illustrates an absorption image 116 of the salami; FIG. 5B illustrates an image 118 of the salami reconstructed using standard integration; FIG. 5C illustrates an image 120 of the salami reconstructed using one dimensional total variation regularization in the image domain; and FIG. 5D illustrates an image 122 of the salami reconstructed using an embodiment of the presently disclosed iterative total variation regularized phase retrieval in the Fourier domain. As shown, the image 122 corresponding to an embodiment of the presently disclosed Fourier domain total variation regularized method has reduced blurring and streak artifacts compared to both the image 118 corresponding to the standard integration method and the image 120 corresponding to the image domain total variation regularization.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is

1. A phase retrieval method for differential phase contrast imaging, comprising:
    receiving data corresponding to a differential phase image generated from a measured signal; wherein the measured signal corresponds to an X-ray signal detected by a detector after passing through a subject located with a grating arrangement between an X-ray source and the detector; and
    generating a phase image corresponding to the integration of the differential phase image, wherein generating the phase image comprises performing an iterative total variation regularized integration in the Fourier domain; wherein the iterative total variation regularized phase retrieval comprises utilizing a regularization term having frequency dependent weighting function.

2. The method of claim 1, wherein the weighting function consists of a first weighting term associated with low frequency characteristics and a second weighting term associated with high frequency characteristics and wherein the first term is substantially greater than the second weighting term.

3. The method of claim 1, wherein the iterative total variation regularized phase retrieval comprises minimizing a residual norm associated with the data and adding one or more regularization terms.

4. The method of claim 1, wherein the iterative total variation regularized phase retrieval comprises an iterative shrinking/thresholding algorithm having a gradient descent step.

5. The method of claim 1, wherein the iterative total variation regularized phase retrieval comprises minimizing total variation in a y-axis direction.

6. An X-ray imaging system for differential phase contrast imaging of a subject, comprising:
    an X-ray source that in operation generates an X-ray beam directed toward the subject;
    a detector that in operation detects at least a portion of the X-ray beam and produces a signal corresponding to the detected portion of the X-ray beam;
    a grating system comprising one or more gratings located between the X-ray source and the detector;
    a controller that in operation receives the signal from the detector and performs a reconstruction of a differential phase image of the subject based on the signal, and generates a phase image corresponding to the integration of the differential phase image, wherein the controller performs an iterative total variation regularized integration in the Fourier domain to generate the phase image; wherein the iterative total variation regularized phase retrieval comprises utilizing a regularization term having frequency dependent weighting function.

7. The system of claim 6, wherein the weighting function consists of a first weighting term associated with low frequency characteristics and a second weighting term associated with high frequency characteristics and wherein the first term is substantially greater than the second weighting term.

8. The system of claim 6, wherein the iterative total variation regularized phase retrieval comprises minimizing a residual norm associated with the signal and adding one or more regularization terms.

9. The system of claim 6, wherein in operation the controller generates a control signal that controls the analyzer grating to be shifted in a direction orthogonal to grating slits of the analyzer grating to a plurality of positions, and the detector detects at least a portion of the X-ray beam and produces a signal corresponding to the detected portion of the X-ray beam at each of the plurality of positions.

10. The system of claim 6, wherein the analyzer grating is located between the phase grating and the detector.

11. The system of claim 6, wherein the X-ray source comprises an incoherent X-ray source.

12. An image reconstruction method for differential phase contrast imaging, comprising:
    receiving data corresponding to a signal produced by an X-ray detector and corresponding to X-rays that passed through a subject and a grating system to reach the X-ray detector;
    generating a differential phase image of the subject based on the received data; and
    generating a phase image corresponding to the integration of the differential phase image by performing an iterative total variation regularized integration in the Fourier domain to generate the phase image; wherein the iterative total variation regularized phase retrieval comprises utilizing a regularization term having frequency dependent weighting function.

13. The method of claim 12, wherein performing the iterative total variation regularized phase retrieval comprises performing total variation along a y-axis.

14. The method of claim 12, wherein the weighting function consists of a first weighting term associated with low frequency characteristics and a second weighting term associated with high frequency characteristics and wherein the first term is substantially greater than the second weighting term.

15. A non-transitory computer readable medium encoding one or more executable routines, which, when executed by a processor, cause the processor to perform acts comprising:
    performing an image reconstruction of a phase image of a subject based on a signal generated by an X-ray detector based on a detected X-ray beam that passed through a subject and a grating system, wherein performing the image reconstruction comprises generating a differential phase image of the subject based on the signal and performing an iterative total variation regularized phase retrieval in the Fourier domain to generate the phase image from the differential phase image; and wherein the iterative total variation regularized phase retrieval comprises utilizing a regularization term having frequency dependent weighting function.

16. The computer readable medium of claim 15, wherein performing the iterative total variation regularized phase retrieval comprises performing total variation along an x-axis and a y-axis.

17. The computer readable medium of claim 15, wherein performing the iterative total variation regularized phase retrieval comprises utilizing a regularization term having a first weighting term associated with low frequency characteristics of the data and a second weighting term associated with high frequency characteristics of the data, and the first weighting term is substantially less than the second weighting term.

* * * * *